United States Patent [19]

Brion et al.

[11] Patent Number: 4,879,392

[45] Date of Patent: Nov. 7, 1989

[54] PROCESS FOR MAKING PERHYDROINDOLE-2-CARBONXYLIC ACID

[75] Inventors: Francis Brion, Gagny; Jean Buendia, Le Perreux sur Marne; Christian Marie, Noisy le Sec, all of France

[73] Assignee: Roussel Uclaf, Paris, France

[21] Appl. No.: 111,982

[22] Filed: Oct. 21, 1987

[30] Foreign Application Priority Data

Oct. 22, 1986 [FR] France ............................... 86 14650

[51] Int. Cl.[4] ........................................... C07D 209/18
[52] U.S. Cl. ...................................... 548/492; 548/505
[58] Field of Search ............................. 548/505, 492

[56] References Cited

U.S. PATENT DOCUMENTS 2,315,661 4/1943 Salzev et al. ...................... 548/505
4,156,016 5/1979 Dalton et al. ...................... 548/505

FOREIGN PATENT DOCUMENTS 1209662 10/1970 United Kingdom ................ 548/505

Primary Examiner—David B. Springer
Attorney, Agent, or Firm—Bierman and Muserlian

[57] ABSTRACT

A process for the asymmetric preparation of a compound of the formula

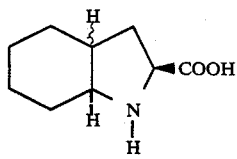

wherein the hydrogen at 3a and 7a are of cis or trans configuration and their non-toxic, pharmaceutically acceptable acid addition salts comprising submitting a compound of the formula

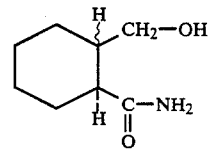

to a Hoffman reaction and reacting the resulting product with formaldehyde in the presence of cyanide ions and acid halide of benzoic acid or an aliphatic carboxylic acid of 1 to 5 carbon atoms to obtain a compound of the formula

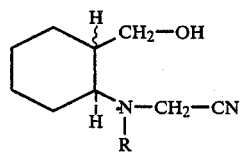

wherein R is acyl of benzoic acid or aliphatic carboxylic acid of 1 to 5 carbon atoms, cyclizing the latter to form a compound of the formula

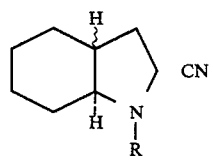

selectively hydrolyzing the latter with a dilute aqueous mineral acid to obtain a compound of the formula

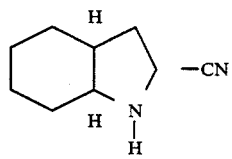

subjecting the latter to hydrolysis with a concentrated aqueous mineral acid to form the acid addition salt of a compound of claim 1 and optionally forming the free base.

7 Claims, No Drawings

PROCESS FOR MAKING PERHYDROINDOLE-2-CARBONXYLIC ACID

STATE OF THE ART

European Patent Application No. 0,084,164 describes the preparation of compounds of the formula

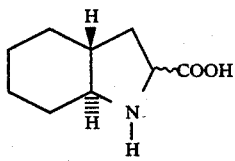

and their use to produce compounds endowed with the ability to inhibit the conversion enzyme of angio-tensine. Tetrahedron Letters, Vol. 24, p. 5343 and p. 5347 (1983) describe the following schematized reaction

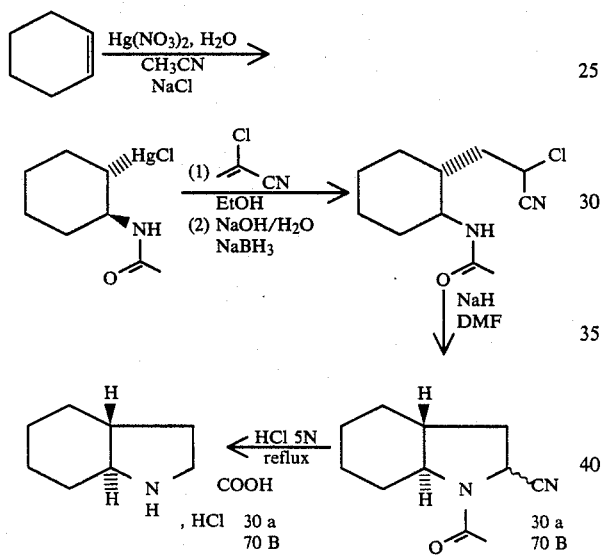

wherein the wavy line indicates the nitrile is an α,β- mixture and the solid line at the 3a carbon indicates that the hydrogen is α- or β-. The synthesis is not useful commercially since it uses mercury in the form of its nitrate in a stoichiometric amount in the first step and in the last step, the nitrile is 20% of the epimer mixture and the same amount is formed in the acid.

Additional related prior art are U.S. Pat. Nos. 4,350,704, 4,425,355 and 4,490,386, Journal of Medicinal Chemistry, Vol. 28, No. 11 (1985) p. 1606–1611 and Tetrahedron Letters, Vol. 24 (1983), p. 5343–5346.

OBJECTS OF THE INVENTION

It is an object of the invention to provide a novel process for the compounds of formula I and to provide novel intermediates therein.

This and other objects and advantages of the invention will become obvious from the following detailed description.

THE INVENTION

The novel process of the invention for the asymmetric preparation of a compound of the formula

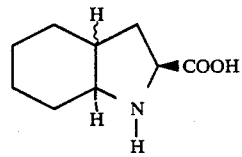

wherein the hydrogen at 3a and 7a are of cis or trans configuration and their non-toxic, pharmaceutically acceptable acid addition salts comprises submitting a compound of the formula

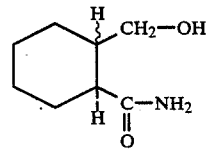

to a Hoffman reaction and reacting the resulting product with formaldehyde in the presence of cyanide ions and acid halide of benzoic acid or an aliphatic carboxylic acid of 1 to 5 carbon atoms to obtain a compound of the formula

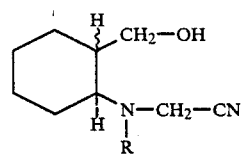

wherein R is acyl of benzoic acid or aliphatic carboxylic acid of 1 to 5 carbon atoms, cyclizing the latter to form a compound of the formula

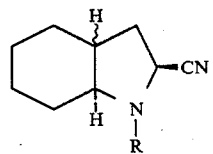

selectively hydrolyzing the latter with a dilute aqueous mineral acid to obtain a compound of the formula

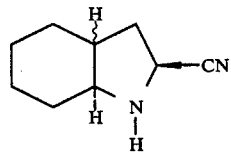

subjecting the latter to hydrolysis with a concentrated aqueous mineral acid to form the acid addition salt of a compound of claim 1 and optionally forming the free base.

Examples of suitable acids for the acid addition salts are inorganic acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid, aspartic acid, alkane sulfonic acids such as methane sulfonic acid or ethane sulfonic acid or arylsulfonic acids such as benzene sulfonic acid or p-toluene sulfonic acid and arylcarboxylic acids such as benzoic acid.

By a process of asymmetric preparation, it is understood that the absolute configurations of the 3a and 7a carbons are preserved in the course of the process. It is thus for example that a derivative of the formula II 3a(R)trans leads to a derivative with the formula I 3a(R)trans. The present application aims at the preparation of both cis and trans products, and preferably the latter, in particular 3aR.

The Hofmann reaction leading to the decarbonylated derivative of formula II is carried out under standard conditions [cf. for example Merck Index 9th Ed. p. ONR 45]. The formaldehyde is preferably used as is but may be used in a bisulfite combination, or further polymerized, particularly in the paraformaldehyde form. The cyanide ions are preferably used as an alkali metal cyanide such as sodium cyanide or preferably potassium cyanide.

The aliphatic acyl halide or benzoyl halide is an iodide, a bromide, or preferably a chloride. The aliphatic acyl has 1 to 5 carbon atoms, but preferably 2 or 3. A benzoyl halide is preferably used, particularly the chloride. All these operations are preferably used in the sam container without isolating the reaction intermediates, but these can be isolated, if desired.

The cyclization of the compound of formula III is carried out preferably by reaction with an alkyl sulfonyl halide or an alkylphenylsulfonyl halide, followed by the action of a strong base. The alkylsulfonyl halide can be an iodide, a bromide, and preferably a chloride and the alkyl may have 1 to 3 carbon atoms, and preferably only 1. Methanesulfonyl chloride (or mesyl chloride) is preferred.

The alkylphenylsulfonyl halide can be an iodide, a bromide, and preferably a chloride as the alkyl may have 1 to 3 carbon atoms, and preferably only 1. There can be cited in particular (4-methylphenyl) sulfonyl chloride (or tosyl). The strong base is preferably an alkali metal hydride such as potassium hydride, and in particular sodium hydride. Other bases can also be used such as an alkali metal alcoholates, preferably potassium tertbutylate.

The hydrolysis of the compounds of formula IV in two stages enables the desired isomer to be obtained with a yield of 80 to 98%, starting with a compound of formula IV in which the desired isomer is in the proportion of 0 to 70% only. In the first stage for selectively hydrolyzing the amide, for example, between 1.5 and 3.0 equivalents, preferably about 2.5 equivalents of a dilute mineral acid such as sulfuric acid, hydrobromic acid, and in particular hydrochloric acid are used. The acid is used, for example, in a 1 to 3N concentration and the operation can be done at a temperature less than or equal to the reflux of the reaction mixture, depending on the concentration of the acid.

In the second stage for hydrolyzing the nitrile, preferably about 2 to 5 equivalents or even more of an acid are added in a more concentrated form and the operation is carried out preferably at reflux of the reaction mixture under a 3N or higher concentration, preferably 5N or 6N. The acid can be different from that used in the first step, but is preferably the same. Under these conditions, starting with a mixture containing 0% of the desired isomer, about 80% of desired isomer is obtained after hydrolysis, while 95% is obtained starting with a mixture containing 70% of desired isomer.

The product of formula I obtained in a salified form can be desalified or salified differently if desired, by standard methods.

In a preferred embodiment of the process, the compound of formula II is prepared either by opening and epimerization of the lactone of the formula

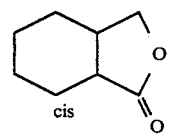

followed by an esterification to obtain a compound of the formula

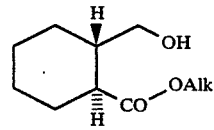

wherein Alk is alkyl of 1 to 5 carbon atoms, which is amidified to obtain the compound of the formula II with the structure

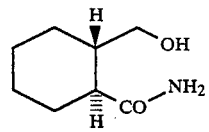

or by simultaneous opening and amidification of said lactone of formula V to obtain the compound of formula II with the structure

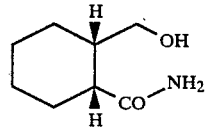

The opening and epimerization of the lactone of formula V may be effected, for example, by the action of a linear or branched secondary amine such as diethylamine, and preferably a cyclized secondary amine such as morpholine, piperidine or particularly pyrrolidine. The operation is preferably effected in the presence of a catalytic amount of an alkali metal alcoholate of 1 to 5 carbon atoms, particularly sodium methylate, in a solvent such as the alkanol corresponding to the alkali metal alcoholate.

The esterification is carried out preferably by dissolution in the alkanol chosen for the esterification such as isopropanol, propanol and particularly ethanol and quite particularly methanol, in a mineral or organic acid medium such as concentrated sulfuric acid or p-toluene sulfonic acid. The amidification is done with concentrated ammonia. The opening of the lactone and the simultaneous amidification are carried out with concentrated ammonia.

The product of formula V is known. [See Kennewell et al., Journal of Chemical Soc., Perkin I, (1982), p. 2563].

In other preferred conditions, the product of formula V is prepared from the anhydride of the formula

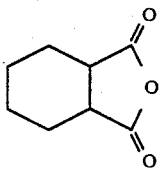 VII either by the action of an excess of an alkanol of 1 to 5 carbon atoms to obtain a compound of the formula

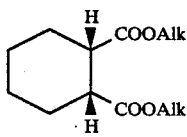 VIII wherein Alk has the significance already indicated, which is submitted to the action of pig's liver esterase to obtain a compound of the formula

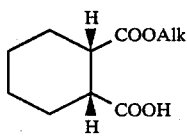 IX wherein Alk has the significance already indicated, which is reduced by the action of sodium in ammonia or of sodium diethyldihydroaluminate to obtain the compound of the formula

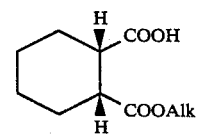 X wherein Alk has the significance already indicated, which is reduced with an alkali metal borohydride after the action of alkyl haloformate of 1 to 3 alkyl carbon atoms to obtain the compound of formula V.

The reaction of the anhydride of formula VII with the alkanol in excess is carried out preferably in the presence of a mineral acid such as hydrochloric acid, and preferably sulfonic acid. About 2 moles of alkanol are reacted per mole of anhydride. The reaction of the compound of formula VIII with the pig's liver esterase is carried out for example under the conditions described inn Angew. Chem., Int. Ed. Engl. Vol. 23, (1984), No. 1, pg. 67–68.

The compounds of formulae IX and X are separated preferably by chemical resolution and more preferably by crystallization of the diastereoisomeric salts with right or left dimethyl bases of chloramphenicol.

The novel intermediates of the invention are the compounds of formulae

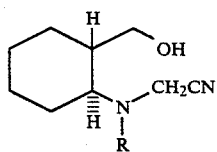 III

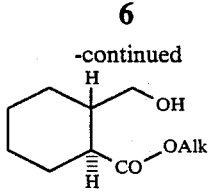 VI wherein R and Alk have the above definitions.

The process and intermediates of the present application are useful to prepare inhibitors of the conversion enzyme of angiotensine of the formula

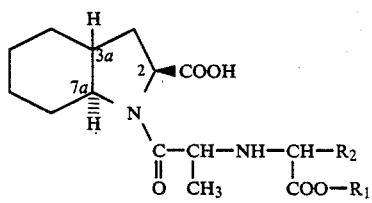

wherein $R_1$ is alkyl of 1 to 6 carbon atoms, preferably ethyl and $R_2$ is alkyl of 1 to 6 carbon atoms, preferably 1 to 4, or phenyl, $R_2$ is most preferably propyl or phenethyl, and where the hydrogen at 3a is in position 3α-(cis derivatives) or in particular 3α-(trans derivatives).

In the following examples there are described several preferred embodiments to illustrate the invention. However, it should be noted that the invention is not intended to be limited to the specific embodiments.

EXAMPLE 1

[2RS (2a,3a , 7a β)] octahydro-1H-indol-2-carboxylic acid hydrochloride STEP A: Dimethyl ester of meso cis 1,2-cyclohexane dicarboxylic acid 100 g of hexahydrophthalic anhydride in 78 ml of methyl orthoformate and 325 ml of methanol were refluxed for 20 hours in the presence of 2.6 ml of concentrated sulfuric acid to obtain 123.3 g of dimethyl ester of meso cis 1,2-cyclohexane dicarboxylic acid.

STEP B: Monomethyl ester of (1S,cis) 1,2-cyclohexane dicarboxylic acid 70 g of the product of Step A in 175 ml of water and 175 ml of phosphate buffer [pH=7 (0.2M)] was taken to 30° C. with 4 ml of pork liver esterase (40 mg) with stirring for 48 hours while maintaining the pH at 7 by addition of N sodium hydroxide. 3 ml of esterase were added and then a further 3 ml after 96 hours. After 120 hours, extraction was done with ethyl acetate and the mother liquors were acidified to pH=2 with concentrated hydrochloric acid, then extracted with ethyl acetate. By drying filtering, and evaporating to dryness under reduced pressure, 61 g of monomethyl ester of (1S,cis) 1,2-cyclohexane dicarboxylic acid melting at less than 50° C. were obtained.

STEP A': Monomethyl ester of (dl, cis) 1,2-cyclohexane dicarboxylic acid 30 g of hexahydrophthalic anhydride in 300 ml of methanol were refluxed for 2 hours 30 minutes and then was evaporated to dryness under reduced pressure. The residue was chromatographed over silica (eluent: cyclohexane—ethyl acetate, 6-4) and crystallized from hexane to obtain 32.6 g of monomethyl ester of (dl, cis) 1,2-cyclohexane dicarboxylic acid.

STEP B'1: Monomethyl ester of (1S,cis) 1,2-cyclohexane dicarboxylic acid 2.883 g of right dimethyl base of chloramphenicol were added to a solution of 2.235 g of the product of Step A' in 40 ml of methylene chloride and 40 ml of ethyl acetate were added. The methylene chloride was distilled off under reduced pressure to obtain 2.655 g of crystallized product which was dissolved in methylene chloride. Ice was added with about 80 ml of 0.1N hydrochloric acid, and extraction was done with methylene chloride. The extracts were evaporated to dryness, then crystallized from hexane at −60° C. to obtain 0.87 g of monomethyl ester of (1S, cis) 1,2-cyclohexane dicarboxylic acid melting at 50° C. and having a specific rotation of $[\alpha]_D^{20} = +4°$ (c=1% in methanol).

STEP B'2: Monomethyl ester of (1R,cis) 1,2-cyclohexane dicarboxylic acid

The operation of Step B' was repeated with 2.402 g of left dimethyl base of the chloramphenicol and 1.862 g of the product of Step A' to obtain 2.216 g of product in the form of the salt of the optical base. Starting with the salt obtained, 0.736 g of monomethyl ester of (1R,cis) 1,2-cyclohexane dicarboxylic acid were obtained which melted at 50° C. and had a specific rotation of $[\alpha]_D^{20} = -6°$ (c=0.3% in methanol).

STEP C: (3aS, cis) hexahydro 1-(3H)-isobenzofuranone

Variant 1:

400 ml of ammonia were condensed to −65° C. and a solution of 14.6 g of the product of Step B or B'1 in 60 ml of ethanol were added. Then under agitation and by fractions, 18 g of sodium were added and stirring was continued for a further 30 minutes after the introduction was finished. Then, 120 ml of ethanol were added slowly and the ammonia was allowed to evaporate for 16 hours. The white solid obtained was dissolved by addition first of 60 ml of ethanol, then of ethyl acetate and then of water. After acidifying with 68 ml of concentrated hydrochloric acid, extraction was done with ethyl acetate. The extracts were washed, dried and concentrated to dryness to obtain 5.5 g of residue which was taken to reflux in 70 ml of toluene with 165 mg of p-toluene sulfonic acid. The mixture was distilled to eliminate the water, then cooled, and ice and sodium bicarbonate were added. Extraction was done with ethyl acetate an the extracts were washed, dried, filtered, taken to dryness and purified by chromatography over silica (eluent: cyclohexane—ethyl acetate) to obtain 2.9 g of (3aS, cis) hexahydro 1-(3H)-isobenzofuranone with a boiling point of 70° C. under 1 mm of mercury and a specific rotation of $[\alpha]_D^{20} = -26.5°$ (c=1.5% in methanol).

Variant 2:

At −5° C. and over a few minutes, a solution of 256 mg of ethyl chloroformate in 0.6 ml of tetrahydrofuran was added to a solution of 440 mg of the product of Step B'2 and 239 mg of triethylamine in 3.3 ml of tetrahydrofuran. The mixture was stirred for 30 minutes and then the precipitate was filtered off. The filtrate was added dropwise to a suspension of 235 mg of 95% sodium borohydride in 2.3 ml of water maintained at about 12° C. which was then left for 3 hours 30 minutes at ambient temperature. It was then cooled, acidified with 2N hydrochloric acid and extracted with methylene chloride. The extracts were dried, evaporated to dryness, purified by chromatography over silica (eluent: cyclohexane ethyl acetate, 65–35) to obtain 228 mg of (3a S, cis) hexahydro 1-(3H)-isobenzofuranone with a specific rotation of $[\alpha]_D^{20} = -47°$ (c=0.6% in chloroform).

STEP D: N-(cyanomethyl)-N-[(trans)-2-hydroxymethylcyclohexyl] benzamide Hofmann degradation Under an inert atmosphere and over 10 minutes, 3.6 ml of bromine were added at 5° C. to 60 ml of 5N sodium hydroxide and the solution was stirred at 5° C. for 15 minutes. Then, 10 g of (1S, trans) 2-(hydroxymethyl cyclohexane-carboxamide were added with stirring for 15 minutes and the refrigerating bath was removed after which stirring was continued for a further 30 minutes. Then, the reaction mixture was placed in an oil-bath heated to 75° C. for 30 minutes and then cooled to 10° C. The pH was adjusted to 7 by careful introduction of 17 ml of 36° Be concentrated hydrochloric acid and then 4.4 ml of a 40% solution of formol in water and 4.15 g of potassium cyanide were added. The mixture was stirred at ambient temperature for 5 hours, then at 5° C. for 16 hours. After this, 8 g of sodium carbonate, 50 ml of ethyl acetate and 8.5 ml of benzoyl chloride were added at 20° C. followed by stirring for 20 minutes, filtering and extracting with ethyl acetate. The extracts were washed with water, dried, filtered and evaporated to dryness under reduced pressure. The residue was purified by chromatography over silica (eluent: cyclohexane-ethyl acetate 1—1) to obtain 7.76 g of N-(cyanomethyl)-N[(trans)-2-hydroxymethylcyclohexyl] benzamide melting at 113° C. after crystallization from isopropyl ether.

STEP E: 1-benzoyl-octahydro-1N-indol-2-carbonitrile

With stirring under an inert atmosphere, a solution of 7.2 g of the product of Step D in 36 ml of tetrahydrofuran was cooled to 5° C. and 4.3 ml of triethylamine and then 2.37 ml of methane sulfonyl chloride was added. The mixture was stirred for 1 hour at 5° C. and then 14.4 ml of dimethylformamide and 5.25 g of 50% sodium hydride were added with stirring for 16 hours at 20° C. After cooling to 5° C, little by little, 10 ml of a mixture of equal parts of water and tetrahydrofuran were added, followed by dilution with ethyl acetate, pouring in to 100 ml of monosodium phosphate, filtering and extracting with ethyl acetate. The extracts were washed with water, dried, filtered and evaporated to dryness under reduced pressure to obtain 9.4 g of product which was purified by chromatography on silica (eluent: cyclohexane—ethyl acetate, 1—1) to obtain 4.43 g of 1-benzoyl-octahydro-1N-indol-2-carbonitrile melting at 125° C. after crystallization from isopropyl ether. By crystallizing from methylene chloride—isopropyl ether 2-5, the product obtained was 96% of the epimer containing the CN radical in β and 4% of the α melting at about 135° C. Variant of Step E carried out in two stages by isolating the intermediate derivative.

The operation was done as above using as solvent 10 volumes of methylene chloride but with stirring for 2 hours 30 minutes at 5° C. The intermediate N-(cyanomethyl)-N-[(trans)]-3-methylsulfonyloxymethyl-cyclo- hexyl-benzamide melting at 115° C. after crystallizing from isopropyl ether. After treatment with sodium hydride in dimethylformamide, the expected product was obtained melting at 115° C. [β-CN: 70% α CN - 30%)],

STEP F: [2RS (2a,3a α, 7a β)]-octahydro-1H-indol-2-carboxylic acid hydrochloride With stirring under an inert atmosphere, 500 mg of the product of Step E (mixture of CN β-CN α 70-30) were dissolved in 1.5 ml of dioxane and 0.95 ml of 36° Be concentrated hydrochloric acid diluted 50% were added with stirring for 90 minutes at reflux (about 92° C). 0.42 ml of concentrated hydrochloric acid were introduced, and the mixture was refluxed for 1 hour and then cooled to ambient temperature and diluted with 1 ml of water. The benzoic acid was eliminated by extracting twice, each time with 5 ml of ethyl acetate. After washing with 0.5 ml of water, the aqueous phases were evaporated to dryness and entrainment was done with methylene chloride. By taking up with methylene chloride, separating, washing and drying at 20° C. under reduced pressure, 465 mg of [2RS (2a,3a α, 7a β)]-octahydro-1H-indol-2-carboxylic acid hydrochloride were obtained, β-CO₂H=96%. By operating as above but starting with a product from Step E with 100% α-CN, the expected βCO₂H=83% product were obtained.

EXAMPLE 2

(1S,trans) 2-(hydroxymethyl)-cyclohexane carbamide
STEP A: (1S,trans) 1-[(2-hydroxymethyl-1-cyclohexyl)-carbonyl]-pyrrolidine 4 g of (3aS,cis) hexahydro-1-(3H)-isobenzofuranone in 20 ml of methanol and 4.76 ml of pyrrolidine with 0.386 g of sodium methylate were refluxed for 20 hours and one half of the methanol was distilled off at 50° C. under reduced pressure. Water and ice were added and the pH was adjusted to 1 by adding 2N hydrochloric acid. Extraction was done with methylene chloride and the extracts were washed with water, dried, filtered, evaporated to dryness under reduced pressure and crystallized from isopropyl ether to obtain 3.89 g of (1S,trans) 1-[(2hydroxymethyl-1-cyclohexyl)-carbonyl]-pyrrolidine melting at 115° C.

STEP B: (1S trans) methyl 2-(hydroxymethyl)-cyclohexane carboxylate 790 mg of the product from Step A in 8 ml of methanol and 0.2 ml of sulfuric acid (d=1.84) were refluxed for 8 hours and part of the methanol was distilled off. The remainder was poured into iced water and extracted with methylene chloride. The extracts were washed with water, dried, filtered and taken to dryness under reduced pressure, then purified by chromatography over silica (eluent: methylene chloride: ethyl acetate 9-1)to obtain 506 mg of (1S trans) methyl 2-(hydroxymethyl)-cyclohexane carboxylate with a specific rotation of $[\alpha]_D^{20}=+27.5°$ (c=0.5% in chloroform).

STEP C: (1S, trans) 2-(hydroxymethyl) cyclohexane carboxamide 200 mg of the product of Step B were stirred for 16 hours in 2 ml of concentrated ammonia, then centrifuged, and the precipitate was dissolved in methylene chloride with 10% of methanol. The solution was concentrated to dryness and the residue was taken up with isopropyl ether, concentrated to a small volume, separated and washed with very little isopropyl ether to obtain 134 mg of (1S, trans) 2-hydroxymethyl) cyclohexane carboxamide melting at 170° C. and having a specific rotation of $[\alpha]_D^{20}=+45°$ (c=0.9% in methanol).

Preparation of (1S,cis) 2-(hydroxymethyl) cyclohexane carboxamide 250 mg of (3aS, cis) hexahydro-1-(3H)-isobenzofuranone were stirred for 24 hours at ambient temperature in 2.5 ml of 28° Be concentrated ammonia and the precipitate formed was separated, dried, for 150 mg of (1S,cis) 2-(hydroxymethyl) cyclo hexane carboxamide melting at 153° C. The cis product, treated as indicated in Example 1, leads to the corresponding (3a,7a) cis derivative.

Various modifications of the processes and intermediates of the invention may be made without departing from the scope thereof and it is to be understood that the invention is intended to be limited only as defined in the appended claims.

What we claim is:
1. A process for the asymmetric preparation of a compound of the formula

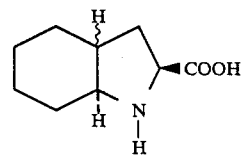

wherein the hydrogens at 3a and 7a are of cis or trans configuration and their non-toxic, pharmaceutically acceptable acid addition salts consisting essentially of submitting a compound of the formula

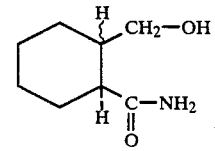

to a Hoffman reaction and reacting the resulting product with formaldehyde, cyanide ions and an acid chloride, bromide or iodide of benzoic acid or an alkyl carboxylic acid of 1 to 5 carbon atoms to obtain a compound of the formula

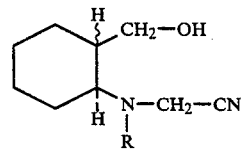

wherein R is acyl of benzoic acid or alkyl carboxylic acid of 1 to 5 carbon atoms, cyclizing the latter to form a compound of the formula

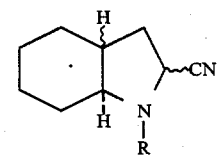

selectively hydrolyzing the latter with a dilute aqueous mineral acid to obtain a compound of the formula

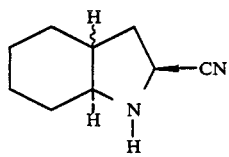

IV' and subjecting the latter to hydrolysis with a concentrated aqueous mineral acid to form the acid addition salt of a compound of Formula I.

2. The process of claim 1 wherein the 3a and 7a hydrogens are of trans configuration.

3. The process of claim 1 wherein the acid halide is benzoyl chloride.

4. The process of claim 1 wherein the cyclization of the compound of formula III is effected with alkylsulfonyl halide or alkylphenyl sulfonyl halide followed by a strong base treatment.

5. The process of claim 1 wherein the compound of formula II is prepared by opening and epimerization of a lactone of the formula

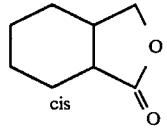

V esterifying the latter to form a compound of the formula

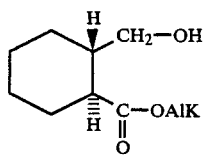

VI wherein Alk is alkyl of 1 to 5 carbon atoms and amidifying the latter to form the compound of the formula

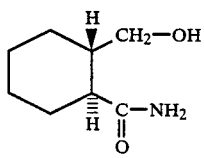

IIA

6. The process of claim 5 wherein the opening and epimerization is effected with a secondary amine in the presence of an alkali metal alcoholate of 1 to 5 carbon atoms, the esterification is effected with an alkanol of 1 to 5 atoms in an acid medium and the amidification is effected with concentrated ammonia.

7. The process of claim 1 wherein the compound of Formula I is reacted with a base to form the free base.

* * * * *

UNITED STATES PATENT AND TRADEMARK OFFICE
CERTIFICATE OF CORRECTION

PATENT NO. : 4,879,392

DATED : Nov. 7, 1989

Page 1 of 2

INVENTOR(S) : FRANCIS BRION, JEAN BUENDIA and CHRISTIAN MARIE

It is certified that error appears in the above-identified patent and that said Letters Patent is hereby corrected as shown below:

On the title page:
Item [54] and
Column 1, lines 2 & 3

"PROCESS FOR MAKING PERHYDROINDOLE-2-CARBONXYLIC ACID" should be

--PROCESS FOR MAKING PERHYDROINDOLE-2-CARBOXYLIC ACID--

Item [57]  Abstract

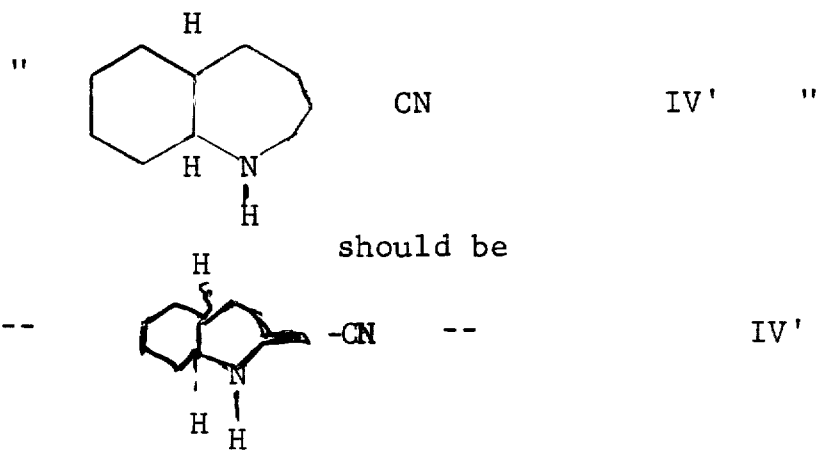

Col. 1   Line 43   "30a       should be  --30α
                    70B"                   70β -- (both occurrences).

UNITED STATES PATENT AND TRADEMARK OFFICE
CERTIFICATE OF CORRECTION

PATENT NO. : 4,879,392

DATED : Nov. 7, 1989

INVENTOR(S) : FRANCIS BRION, JEAN BUENDIA and CHRISTIAN MARIE

It is certified that error appears in the above-identified patent and that said Letters Patent is hereby corrected as shown below:

| Col. | Line |  |
|---|---|---|
| 8 | 17&18 | "10° C" should be --10°C-- |
| 9 | 7&8 | "36° Be " should be --36° Bé-- |
| 9 | 9&10 | "92° C" should be --92°C-- |

Signed and Sealed this

Nineteenth Day of March, 1991

Attest:

HARRY F. MANBECK, JR.

Attesting Officer

Commissioner of Patents and Trademarks